United States Patent [19]

LeGault et al.

[11] Patent Number: 4,639,254
[45] Date of Patent: Jan. 27, 1987

[54] THREE-DIMENSIONAL SANITARY NAPKIN HAVING ABSORBENT MATERIAL CONTOURED ON THE BAFFLE SIDE

[75] Inventors: Robert H. LeGault, Neenah, Wis.; Arrigo D. Jezzi, Roswell, Ga.; James D. Milner, Appleton, Wis.; Barbara Oakley; Paul G. Franke, both of Menasha, Wis.

[73] Assignee: Kimberly-Clark Corporation, Neenah, Wis.

[21] Appl. No.: 790,702

[22] Filed: Oct. 24, 1985

[51] Int. Cl.⁴ .................................. A61F 13/16
[52] U.S. Cl. ........................................ 604/385 R
[58] Field of Search .............. 604/385.1, 386, 387, 604/358

[56] References Cited

U.S. PATENT DOCUMENTS

| | | | |
|---|---|---|---|
| D. 215,386 | 9/1969 | Glassman | D83/1 |
| D. 236,385 | 8/1975 | Celander | D83/1 A |
| D. 272,190 | 1/1984 | Sneider | D24/51 |
| D. 276,554 | 11/1984 | Glassman | D24/51 |
| 2,331,355 | 10/1943 | Strongson | 604/385 |
| 2,747,575 | 5/1956 | Mercer | 604/385 |
| 2,964,039 | 12/1960 | Johnson, Jr. et al. | 128/290 |
| 2,973,760 | 3/1961 | Dudley | 128/287 |
| 3,406,689 | 10/1968 | Hicks et al. | 128/290 |
| 3,463,154 | 8/1969 | Hendricks | 128/287 |
| 3,528,422 | 9/1970 | Hodas | 604/385 |
| 3,570,491 | 3/1971 | Sneider | 128/290 |
| 3,575,174 | 4/1971 | Mogor | 604/385 |
| 3,677,249 | 7/1972 | Kokx | 128/290 |
| 3,805,790 | 4/1974 | Kaczmarzyk | 128/290 |
| 3,828,786 | 8/1974 | Cervantes | 128/290 |
| 3,857,394 | 12/1974 | Alemany | 128/260 |
| 3,897,784 | 8/1975 | Fitzgerald | 128/290 |
| 3,993,074 | 11/1976 | Murray et al. | 128/286 |
| 4,046,147 | 9/1977 | Berg | 604/385 |
| 4,059,114 | 11/1977 | Richards | 128/287 |
| 4,321,924 | 3/1982 | Ahr | 128/287 |
| 4,333,466 | 6/1982 | Matthews | 604/387 |
| 4,340,058 | 7/1982 | Pierce | 128/287 |
| 4,405,326 | 9/1983 | Lenaghan | 128/290 |
| 4,433,972 | 2/1984 | Malfitano | 604/385 |
| 4,490,147 | 12/1984 | Pierce | 604/378 |

FOREIGN PATENT DOCUMENTS

| | | |
|---|---|---|
| 1581162 | 5/1977 | United Kingdom . |
| 2048684 | 12/1980 | United Kingdom . |
| 2082643 | 3/1982 | United Kingdom . |
| 2133987 | 8/1984 | United Kingdom . |

*Primary Examiner*—John D. Yasko
*Attorney, Agent, or Firm*—P. A. Leipold; D. L. Traut; J. J. Duggan

[57] ABSTRACT

A three-dimensionally hourglass-shaped sanitary napkin with a cellulose fluff insert for absorption that is outwardly bulging on the baffle side to create a thicker region near the center of the sanitary napkin. The baffle or fluid-impervious layer wraps around the absorbent cellulose fluff insert to form a well thereby maintaining fluid within its borders to afford increased protection from fluid leakage.

15 Claims, 4 Drawing Figures

THREE-DIMENSIONAL SANITARY NAPKIN HAVING ABSORBENT MATERIAL CONTOURED ON THE BAFFLE SIDE

TECHNICAL FIELD

The present invention relates, generally, to the field of sanitary napkins for personal feminine care or protection in order to absorb or otherwise contain menstrual fluids or similar exudate, perhaps urine, as a consequence of minor incontinence, or the like. The present invention relates more especially to sanitary napkins which are shaped or contoured in order to improve comfort and absorbency. Most particularly, the present invention concerns an hourglass-shaped sanitary napkin with an absorbent insert that is outwardly bulging on the baffle side to create a thicker region in the middle of the napkin.

DESCRIPTION OF THE BACKGROUND ART

All manner and variety of devices or appliances configured for the absorption of such body fluids as menses are known. Feminine napkins presently used for catamenial protection comprise absorbent pad structures which for the most part are of elongate and substantially rectangular configuration. However, the market is provided with a large variety of such napkins in different lengths, widths, and thicknesses, each of which is designated as being suitable for a particular body size or shape, for heavy or light flows, or for different age needs. In addition to the more common rectangular form, there exists a limited selection of other geometric configurations also designed to meet particular body shapes or sizes.

As a class, sanitary napkins ought to possess certain necessary attributes of absorbency, comfort and psychological as well as physiological or physical protection. Desirably, these devices also are characterized as being discreet during wear.

Sanitary napkins, including contoured sanitary napkins, such as those described in U.S. Pat. Nos. 4,397,644 and 4,079,739, are well known. Conceptualizing, sanitary napkins of this sort are typically of multilayered construction including a fluid absorbent core interposed within a backing of a fluid impermeable shield or baffle and a fluid permeable cover, the latter transmitting menstrual fluid, or the like, across its boundary to the absorbent core. As those skilled in the art will readily appreciate, the interrelationship of components is substantially more intricate; however, for purposes of basic understanding, the foregoing suffices.

The prior art has recognized the practicality of raising one or more layers of the absorbent portion of the sanitary napkin in the direction of the wearer of multilayer sanitary napkins to obtain less fluid leakage, better positioning of the sanitary napkin, and the like. U.S. Pat. No. 2,964,039 discloses a sanitary napkin wherein the napkin has a curved lengthwise configuration giving the napkin a preformed arcuate shape in the direction of its length to conform to and cover the exterior female pubic area. That patent describes sanitary napkins which have a preformed arcuate shape and have a thicker absorbent layer in the middle of the pad than at the ends.

Recognizing the benefit of increasing the amount of the absorbent component in the perineal area of the wearer, U.S. Pat. No. 3,406,689 describes a sanitary napkin comprising two separate pieces. One portion is a replaceable highly-absorbent soft contact pad which actually contacts the body of the wearer. The second portion is a back-up sanitary napkin which is worn by the wearer to keep the contact pad in place. The back-up sanitary napkin is larger and movable with respect to the contact pad and is designed to absorb any excess menstrual discharge.

U.S. Pat. No. 3,528,442 uses a secondary layer centrally located on the top layer of the primary pad. The primary pad has three layers of absorbent fluff and creped wadding and absorbent paper. A wrapping is used to attach the secondary layer to the primary pad. U.S. Pat. No. 4,433,972 offers a similar type of sanitary napkin comprising a backing sheet and a face sheet having an absorbent pad assembly sandwiched between the two sheets. The pad assembly includes two pads. The primary pad is relatively large and is made of wood fluff or similar absorbent material. The second pad is substantially diamond shaped and is of lesser dimensions than the primary pad. The second pad is seated on the primary pad.

Thus, the art has recognized the benefits of increasing the area of absorbent material near the center of the sanitary napkin. U.S. Pat. Nos. 2,331,355, 2,747,575 and 4,046,147 disclose additional means whereby a larger amount of absorbent material is present in the center of the sanitary napkin.

A different method of increasing the bulk or density of absorbent material in a sanitary napkin is described in U.S. Pat. Nos. 4,340,058 and 4,490,147 where a plurality of elongate absorbent pads, each of approximately circular cross-section, are arranged parallel to one another in a pyramid shaped bundle to obtain increased absorbency where most desired in the center of the sanitary napkin.

A sanitary napkin wherein the absorbent material in the center of the sanitary napkin gradually decreases or tapers near the end of the sanitary napkin is disclosed in U.S. Pat. No. 2,973,760. The tapering of the absorbent material is gradual instead of step-wise as was the case for much of the aforedescribed prior art.

Unlike much of the prior art where the sanitary napkin is rectangular or somewhat triangular in shape, U.S. Pat. No. 3,805,790 discloses an anatomy-conforming feminine napkin which is biconcave, that is, substantially hourglass-shaped.

Design U.S. Pat. Nos. 215,386, 236,385, 272,190 and 276,554 depict catamenial napkins wherein there is a raised portion in the center area of the napkin. The raised portions depicted are either folds in the napkin or are the result of an increased amount of absorbent material extending upward to the cover or top layer of the pad.

DESCRIPTION OF THE INVENTION

It has now been determined in accordance with the present invention that an improved feminine sanitary napkin can be provided comprising an absorbent pad of a predetermined, substantially ellipsoidal shape adapted to be removably attached to a supporting garment by adhesive means. The napkin is essentially hourglass-shaped and is made of conventional materials, i.e., a highly absorbent or superabsorbent core of fibrous material or the like, a fluid-pervious cover member, and a fluid-impervious backing member also referred to as a baffle, with pressure sensitive attachment means disposed thereon. The subject invention involves contouring or outwardly bulging the absorbent material, that is, the fluff insert, on the baffle side to create a thicker region near the center of the hourglass. The tapering of the contoured absorbent material toward the distant ends of the sanitary napkin is accomplished by a decrease of the absorbent material. Advantageously, the sanitary napkin of the present invention, and specifically the absorptive core thereof which is contoured on the baffle side, achieves considerably improved fluid distribution and retention. Further advantageous, as a particular consequence of a novel configuration, the sanitary napkin of the present invention has less absorbent material in the ends of the sanitary napkin thereby providing improved discreetness for the wearer. The end result is an excellent combination of protection and comfort.

The foregoing, and other advantages of the present invention, are realized in an essentially biconcave or hourglass-shaped sanitary napkin wherein the absorbent material or absorbent matrix is such that it is contoured or outwardly bulging in the direction of the fluid-impervious backing member or baffle of the sanitary napkin.

The fluid-impermeable baffle or shield which is on the garment sides of the sanitary napkin advantageously forms a well. That is, the baffle advantageously wraps around the fluff insert or absorbent material to make a reservoir thus holding the fluid within its structure to minimize leaking onto the wearer's surrounding garments.

The fluid-pervious cover member is designed to transmit menstrual fluid into the absorbent portion of the sanitary napkin with minimal or no cover runoff. It has preferably been found that this can be readily accomplished by incorporating a cover which is primaraily a nonwoven thermoplastic web having a sufficiently open structure to enhance the transfer of menses to the absorbent matrix. The absorbent matrix contains a principal absorbent component and a second component having comfort enhancement capabilities. The cover of the sanitary napkin is integrated with the comfort enhancement layer at discreet intervals particularly in the perineal area of the napkin. These integration sites are the transfer portions of the sanitary napkin.

Other advantages of the present invention in terms of both construction and mode of operation will be gained from an examination of the following detailed description of preferred embodiments, taken in conjunction with the figures of drawing.

DETAILED DESCRIPTION OF THE PREFERRED EMBODIMENTS

The present invention relates, generally, to the field of sanitary napkins for personal feminine care or protection in order to absorb or otherwise contain menstrual fluids or similar exudate, perhaps urine, as a consequence of minor incontinence, or the like. The present invention relates more especially to sanitary napkins which are shaped or contoured in order to improve comfort and absorbency. Most particularly, the present invention concerns an hourglass-shaped sanitary napkin with a cellulose fluff insert that is contoured or tapered on the baffle side to create a thicker region near the middle of the napkin. Accordingly, the present invention will now be described with reference to certain preferred embodiments within the aforementioned contexts; albeit, those skilled in the art will realize that such a description is meant to be exemplary only and should not be deemed limitative respecting the scope of the present invention, for example in terms of its construction and mode of operation.

Figure 1:
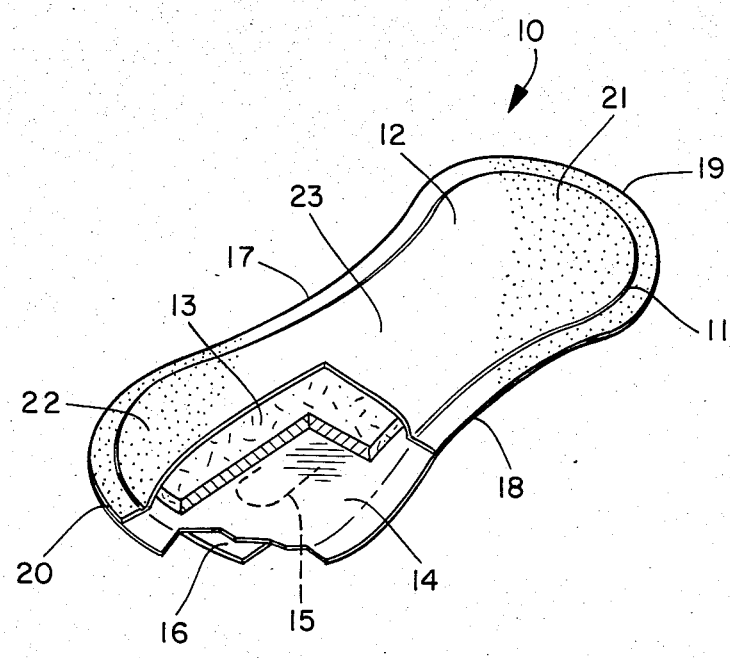
FIG. 1 is a perspective view partly in section of a feminine napkin in accordance with one embodiment of the invention.
Figure 2:
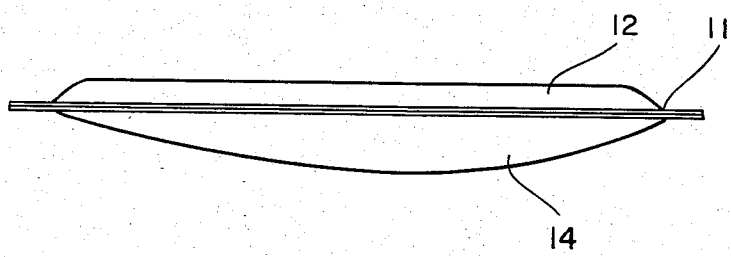
FIG. 2 is a side view of a feminine napkin generally similar to the FIG. 1 embodiment with a cellulose fluff insert that is contoured on the baffle side to create a thicker region near the middle of the sanitary napkin.

Turning to the figures of drawing, in the preferred embodiments of the invention as shown in the accompanying drawings reference is made first to FIGS. 1-2 wherein there is shown an elongate feminine napkin 10 with symmetrically concave side edges 17 and 18. The biconcave or hourglass-shaped napkin 10 is comprised of an absorbent pad body 13, enclosed within a fluid-impervious backing member or baffle 14 and covered by a fluid-pervious cover member 12.

The ends of the pad body may be generally parallel and of equal width while being equally spaced from the minor axis. The minor axis being the narrowest point from side edge 17 to side edge 18. The major axis extends from end edge 19 to end edge 20. The rear end portion 20 of the pad may be shorter and narrower than the front end portion 19. Since the sanitary napkin is hourglass shaped, there are two end lobe regions 21 and 22. The pad is preferably thickest in section at the minor axis, i.e., in the middle region 23 and is tapered down toward each end. The thickness of the rear end portion 20 may taper less than the front end portion 19 to retain substantial thickness for improved absorption in that area. However, in the preferred form the sanitary napkin is symmetrical when considered along its major axis and minor axis.

Figure 4:
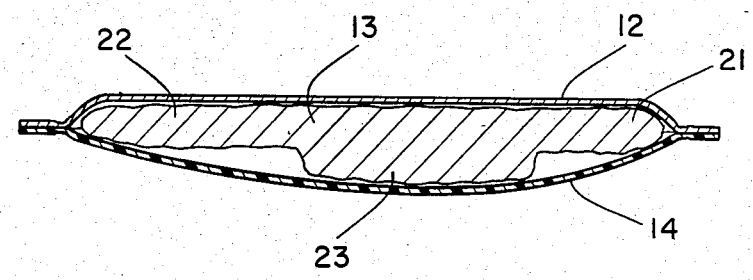
FIG. 4 is another longitudinal cross-sectional view of a sanitary napkin of the present invention where the absorbent material is more distinctly placed near the center of the napkin while remaining outwardly bulging on the baffle side.

In another important structural feature, the fluid-impervious backing member 14 closely adheres to the preshaped pad body, thus providing an impervious fluid-holding container. In FIG. 4, where the absorbent material is prepared in a more step-wise fashion, the fluid-impervious backing member or baffle nevertheless forms a well and closely adheres to the absorbent material. The bottom face of the impervious backing member may have pressure sensitive adhesive means applied thereto and is covered by a protective strip. When this strip is removed, the adhesive serves as the means to attach the napkin to a suitable supporting garment.

The length of the napkin is not critical, but preferably is from about 4 to 11 inches. Larger sizes are not needed for the majority of users because, if larger, the utilization of the available absorbent capacity is grossly inefficient and is therefore wasteful and uneconomical. In addition, longer pads tend to extend outward and are less discreet than shorter sanitary napkins.

Cover member 12 is of the same biconcave contour as absorbent pad body 13. As shown, the edges of cover member 12 extend slightly beyond the entire periphery of the absorbent pad 13. Backing member 14 extends approximately the same distance beyond the entire periphery of the absorbent pad body as cover member 12. Cover member 12 and backing member 14 are directly attached together by fused or sealed line 11. Sealed line 11 may be located at the outside edges of the cover member 12 and backing member 14 or at some distance from the remote edge as depicted in FIGS. 1-2. Anywhere up to ½ inch from the edge of the sanitary napkin is suitable. Sealed or fused line 11 may be formed by ultrasonic bonding or any other method known in the art.

In a preferred embodiment, feminine napkin 10 may have located on the bottom of backing member 14 a strip of pressure sensitive adhesive 15, or the like, covered by a protective release sheet 16. Sheet 16 may be removed to expose adhesive 15 for attachment to a suitable supporting garment. In instances where a tight-fitting undergarment is worn, of course, there is no need for the adhesive, since the close fit of the garment itself will hold the napkin tightly against the body.

As indicated earlier, the elements which make up feminine napkin 10 may consist of known conventional materials. Fluid-pervious cover member 12 may consist of a non-woven thread web, a bonded carded web or absorbent of non-absorbent staple fibers, or an autogeneously or otherwise bonded web of continuous filament synthetic fibers. Many variations of such materials are well known in the art. A preferred cover material is comprised of a hydrophobic, but fluid-permeable, autogeneously bonded web which, due to its hydrophobicity and one-way permeability when in contact with an absorbent pad body, helps provide the napkin with a desirable dry-feeling surface when in use.

Preferably, the cover 12 is similar to that described in U.S. Pat. No. 4,397,644 to Kimberly-Clark Corporation. This patent describes a sanitary napkin with improved comfort and the ability to relatively rapidly transfer menses from the cover into the absorbent pad body. The absorbent pad body or absorbent matrix contains an absorbent component characterized by relatively high fluid retention.

The cover or outer wrap 12 of the napkin of this invention is primarily of a nonwoven thermoplastic web and should be of a sufficiently open structure to enhance the transfer of the viscous fluid menses described above into the transfer layer of the absorbent matrix. For a cover to readily transfer this viscous fluid according to the teachings of this invention it must be sufficiently open to enhance transfer.

The absorbent capacity of the sanitary napkin pad 10 of the present invention is provided by a fluid retentive core or absorbent matrix identified generally as 13. As previously indicated this absorbent body is comprised of a transfer layer and a comfort enhancing layer. In general, the absorbent body 13 may be comprised of any conventional composition or superabsorbent composition including, for example, natural absorbent cellulosic fibers such as wood pulp fluff, cotton, cotton liners, multilayered cellulose wadding, or combinations thereof. It may also include regenerated cellulose fibers or sponge, staple rayon fibers, and various mixtures of absorbency-aiding materials, such as natural or synthetic gums, modified cellulose materials and the like. However, the highly preferred structure for the absorbent body 13 is in the nature of a microfibrous absorbent. More preferably, the absorbent body 13 is comprised of a plurality of individual microfibers. The microfibers are located in an efficient orientation to achieve good capillarity within the target zone to achieve rapid wicking distribution. Preferably the principal absorbent portion comprises primarily cellulosic material.

An important feature of the biconcave or hourglass shaped sanitary napkin of the present invention is the contouring or outward bulging of the absorbent pad on the baffle side of the sanitary napkin. The absorbent pad is preferably a cellulose fluff insert which is contoured such that the cellulose fluff insert is thicker in the region of the middle of the hourglass as depicted in FIG. 2. The amount of the cellulose fluff is decreased as the absorbent pad extends toward the top and bottom of the hourglass. The maximum thickness of the absorbent pad need not be greatest at the exact center or midpoint of the hourglass shaped sanitary napkin. It is only necessary that the greatest amount of cellulose fluff be present at or around the center of the hourglass shaped sanitary napkin. The hourglass configuration of the sanitary napkin is generally symmetrical when considered along its major axis. But the hourglass configuration of the sanitary napkin need not be symmetrical when alternate sides of the napkin are compared across the minor axis. An hourglass shaped sanitary napkin such as that depicted in U.S. Pat. No. 3,805,790 is suitably shaped for purposes of the present invention. Preferably, the hourglass-shaped sanitary napkin is symmetrical when viewed along the major axis and the minor axis.

The tapering of the contoured absorbent material toward the distant ends of the sanitary napkin is accomplished by a decrease of the absorbent material as the cellulose fluff proceeds further from the area of greatest thickness near the center of the hourglass shaped sanitary napkin to the edges 19 and 20. The amount of the absorbent material tapering from the middle region 23 to the end lobes 21 and 22 of the sanitary napkin need not be symmetrical as shown in FIG. 2. Generally, the thickness of the absorbent material in the middle region 23 comprises about 1.5 to about 5 times the thickness of the absorbent material located in the lobe regions 21 and 22. Preferably, the middle region 23 absorbent thickness comprises about 1.75 to about 3.0 times the thickness of the end lobe regions 21 and 22 absorbent. Optionally, the middle region 23 absorbent comprises a density greater than the density of the absorbent in the end lobe regions 21 and 22 of the sanitary napkin. Absorbent body 13 may be manufactured by a variety of techniques.

Figure 3:
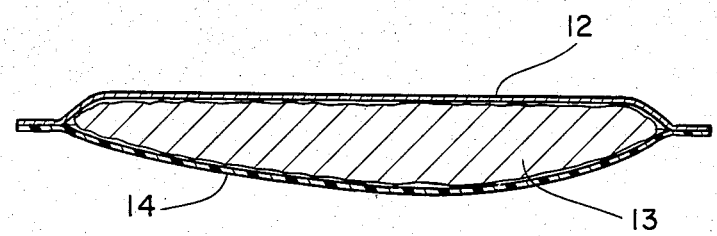
FIG. 3 is a longitudinal cross-sectional view of gradually contoured absorbent material of the sanitary napkin of the present invention.

In FIG. 4, the contouring of the absorbent material is not as gradual as demonstrated in Figure 3. In FIG. 4, there is a sharper delineation once the absorbent material is decreased to provide the bulge on the garment side of the sanitary napkin. Thus, the outward bulge absorbent region is stepped down from the middle region 23 to the end lobe regions 21 and 22.

The absorbent material may be of unibody construction, that is, it may be prepared by being molded. The amount of absorbent material is generally of equal width at and near the center of the hourglass-shaped napkin. However, if desired a slight decrease in the amount of absorbent material near side edge 17 and side edge 18 is possible, if desired.

By contouring the cellulose fluff absorbent insert in this manner, the sanitary napkin has a significantly greater amount of absorbent material in the middle of the pad for improved protection from leakage in the area where it is most needed. In addition, advantageously, decreasing the amount and thickness of absorbent material upon approaching the periphery of the sanitary napkin, that is, the longitudinal or end edges 19 and 20 of the hourglass shape provides increased discreteness for the wearer. The sanitary napkin will not have a tendency to stick out during use. Thus, decreasing the thickness of the absorbent material serves to preserve secrecy because of its inconspicuity when worn.

Fluid impervious backing member 14 is preferably a thin plastic film such as polyethylene or polypropylene of about ½ to 3 mils in thickness. Other thin flexible films such as polyvinyl chloride, polyvinylidene chloride, natural rubber, etc. may be employed. Another useful material is a thin polyurethane foam which may be of open or close-celled construction on the interior, and may be absorbent or nonabsorbent, but which should have a closed fluid-impervious skin on at least the bottom surface.

Exemplary of such a baffle is a conventional 0.4 oz. per square yard spunbond web with a 0.75 mil (0.00075 in.) film of an ethylene methyl acrylate, preferably with the EMA side toward the body of the absorbent material. To that baffle member 14 is secured the absorbent body 13, preferably in the form of two opposed stacks of microfibrous webs.

There is optionally provided a discrete adhesive member 15 for securing the pad 10 to the undergarments of a wearer. This adhesive 15 is most preferably a conventional pressure sensitive adhesive bearing a release paper 16 which may be removed to expose the adhesive 15 for purposes of attachment to the undergarment. The adhesive 15 and associated release paper 16 may be located in a comparatively small singular discreet location or may exist in the form of the more conventional longitudinal strips.

While the invention has now been described with reference to certain preferred embodiments, and exemplified in many respects thereto, those skilled in the art will appreciate that various modifications, substitutions, changes and omissions may be made without departing from the spirit thereof. Accordingly, it is intended that the foregoing description be deemed merely illustrative of certain preferred modes for making and using the present invention and not be deemed limitative on the full scope thereof.

We claim:

1. A three-dimensional hourglass-shaped sanitary napkin comprising a fluid permeable cover with a body contacting surface, an absorbent material adjacent the fluid permeable cover and a fluid impermeable baffle adjacent the alternate side of the absorbent material and having a garment facing surface, said sanitary napkin being substantially hourglass-shaped, comprising (a) two end lobe regions and (b) a middle region, said absorbent material in said middle region being outwardly bulging in said middle region by a greater amount than the absorbent in the end region on the alternate absorbent side adjacent the baffle and wherein said middle region comprises a greater amount of absorbent than said lobe regions.

2. The sanitary napkin of claim 1 wherein said outward bulge absorbent region is stepped down from said middle region to said lobe regions.

3. The sanitary napkin of claim 2 wherein the thickness of said absorbent material located in said middle region comprises about 1.5 to about 5 times the thickness of said absorbent material located in said lobe regions.

4. The sanitary napkin of claim 3 wherein said middle region absorbent thickness comprises about 1.75 to about 3.0 times the thickness of said lobe region absorbent.

5. The sanitary napkin of claim 1 wherein said middle region absorbent comprises a density greater than the density of the absorbent in the lobe regions of said napkin.

6. The sanitary napkin of claim 1 wherein said absorbent material comprises a superabsorbent composition.

7. The sanitary napkin of claim 1 wherein said absorbent material comprises cellulosic material.

8. A sanitary napkin of claim 1 wherein said baffle comprises ethylene methyl acrylate.

9. A sanitary napkin of claim 1 wherein a discreet adhesive member is attached to the garment facing surface of the baffle.

10. A sanitary napkin of claim 9 wherein said discreet adhesive member is in the form of longitudinal strips.

11. The sanitary napkin of claim 1 wherein said absorbent is wood fluff and said greater amount of absorbent in said middle region comprises thicker fluff than the fluff in and said end lobe portions.

12. A sanitary napkin comprising a fluid-permeable bodyside cover, an absorbent material adjacent said fluid-permeable cover and a fluid impermeable outer baffle, wherein (a) said napkin has an hourglass-shape comprising two end lobe regions and a narrower middle region, (b) said narrower middle region is outwardly bulging on the side of said absorbent adjacent said baffle, (c) the absorbent in said middle region is thicker than the absorbent in the end regions, (d) said absorbent is wood fluff, and (e) said middle region is about 1.5 to about 5 times the thickness of said lobe regions.

13. The napkin of claim 12 wherein said middle region is about 1.75 to about 3.0 times the thickness of said lobe region abosorbent.

14. The napkin of claim 1 wherein said baffle in said middle region forms a well in the outwardly bulging portin.

15. The napkin of claim 1 wherein the bodyside surface of said pad is generally planar.

* * * * *